(12) United States Patent
Bosch et al.

(10) Patent No.: US 9,959,639 B2
(45) Date of Patent: May 1, 2018

(54) METHOD OF PTYCHOGRAPHIC IMAGING

(71) Applicant: FEI Company, Hillsboro, OR (US)

(72) Inventors: Eric Gerardus Theodoor Bosch, Eindhoven (NL); Ivan Lazic, Eindhoven (NL)

(73) Assignee: FEI Company, Hillsboro, OR (US)

( * ) Notice: Subject to any disclaimer, the term of this patent is extended or adjusted under 35 U.S.C. 154(b) by 129 days.

(21) Appl. No.: 15/186,267

(22) Filed: Jun. 17, 2016

(65) Prior Publication Data
US 2017/0024908 A1    Jan. 26, 2017

(30) Foreign Application Priority Data
Jun. 18, 2015 (EP) .................................. 15172752

(51) Int. Cl.
| | | |
|---|---|---|
| G06T 11/00 | (2006.01) | |
| G01N 23/04 | (2018.01) | |
| G01T 1/17 | (2006.01) | |
| G02B 21/00 | (2006.01) | |
| H01J 37/22 | (2006.01) | |

(52) U.S. Cl.
CPC ............ *G06T 11/003* (2013.01); *G01N 23/04* (2013.01); *G01T 1/17* (2013.01); *G02B 21/008* (2013.01); *G06T 11/00* (2013.01); *H01J 37/222* (2013.01); *G01N 2223/419* (2013.01)

(58) Field of Classification Search
USPC ................................................. 250/307, 306
See application file for complete search history.

(56) References Cited

U.S. PATENT DOCUMENTS

| | | | |
|---|---|---|---|
| 8,426,831 B2 | 4/2013 | Nihtianov et al. | |
| 9,401,042 B2* | 7/2016 | Rodenburg | A61B 6/027 |
| 9,448,160 B2* | 9/2016 | Maiden | G06T 1/0007 |
| 9,618,332 B2* | 4/2017 | Zhang | G01B 11/14 |
| 2011/0266440 A1 | 11/2011 | Boughorbel et al. | |
| 2012/0140986 A1 | 6/2012 | Maiden | |
| 2013/0228683 A1 | 9/2013 | Boughorbel et al. | |
| 2014/0007307 A1 | 1/2014 | Routh et al. | |
| 2015/0155131 A1 | 6/2015 | Sluijterrnan et al. | |
| 2015/0160450 A1* | 6/2015 | Ou | G02B 21/002 |
| | | | 348/80 |
| 2015/0170876 A1 | 6/2015 | Janssen et al. | |
| 2015/0243474 A1 | 8/2015 | Lazic et al. | |

FOREIGN PATENT DOCUMENTS

WO    2005106531 A1    11/2005

OTHER PUBLICATIONS

Maiden, A., et al. "Superresolution imaging via ptychography", Journal of the Optical Society of America A, Mar. 21, 2011, pp. 604-612, vol. 28, No. 4, OSA Publishing.

* cited by examiner

*Primary Examiner* — Kiet T Nguyen
(74) *Attorney, Agent, or Firm* — Scheinberg & Associates, PC; Michael O. Scheinberg

(57) ABSTRACT

A method and apparatus for ptychographic imaging is described. Typically a high number of pixels (after binning) is needed to obtain a high quality reconstruction of an object. By using calculation planes with more nodes (for example 512×512 nodes) than the number of pixels of the detector, a high quality reconstruction of an object can be made, even when using for example a 16 segment detector, or a 32×32 pixel detector. Although the reconstructed object shows less resolution ("sharpness"), all features are there.

20 Claims, 6 Drawing Sheets

METHOD OF PTYCHOGRAPHIC IMAGING

The invention relates to a method of ptychographic imaging, the method comprising:
  providing an object in an object plane
  providing a pixelated detector in a detector plane, the detector plane conjugated to the object plane by a Fresnel propagator, the detector equipped to detect the intensity of a wave front,
  provide a radiation source and probe forming parts equipped to form an input wave on the object plane,
  provide a first mathematical estimate of the object, an estimate of the Fresnel propagator and an estimate of the radiation probe, the mathematical estimate of the object represented by a number of nodes in a first calculation plane, each node a complex value, the method comprising:
    acquiring at least two images by
    selecting an area of the object for irradiation,
    irradiating the area with radiation,
    detecting the intensity of the resulting wave front on the pixelated detector, resulting in a detector image,
    each irradiated area overlapping with at least one other irradiated area, and iteratively
    updating the mathematical estimate of the object such that, after multiplying the estimate of the object with the estimate of the probe in the first calculation plane and propagating using the Fresnel propagator to a mathematical estimate of the image represented by a number of nodes of a second calculation plane, the detected intensity of a pixel of the detector image matches the intensity of the corresponding area of the mathematical estimate of the image in said second calculation plane for the at least two images, until a break-off criterion is met.

Such a method is known from "Superresolution imaging via ptychography", A. M. Maiden et al., J. Opt. Soc. Am. A, vol 28, no 4 (April 2011), pp 604-612, further referred to as Maiden [-1-].

Maiden describes a ptychographic imaging process. The process comprises two parts: a part of image retrieval and a part of image reconstruction.

The image retrieval part comprises irradiating an object in an object plane with an input wave, forming a number of overlapping irradiated spots. The input wave, after passing through the object, is converted to an output wave that propagates to a diffraction plane, where a pixelated detector in this detector plane detects its (place dependent) intensity. This thus results in a number of images.

The part of image reconstruction comprises an iterative process where, from a first mathematical estimate of the object (the object described by a number of nodes with an associated complex value) and a first guess of the input wave, using a Fast Fourier Transform (FFT), a mathematical estimate of the wave front at the detector plane is made. The modulus of the estimated values of the wave front at the detector, or at least a number of them, are then replaced by the square root of the measured intensity at the corresponding positions, and an inverse FFT is used to transform the image back to the object plane, after which an updated version for the spot and the object are determined.

It is noted that the number of nodes in the mathematical estimate of the wave front at the detector plane may be larger than the number pixels of the detector: part of the nodes may be in an area outside of the physically detected area. The nodes correspond to the pixels in a one-to-one relationship. It might happen that some nodes do not have a corresponding pixel in which case said nodes can either remain unchanged during the replacement phase.

It is noted that other methods of dealing with such pixels can be envisioned, such as setting it to zero. However, this might hamper convergence or it may introduce artifacts.

It is further noted that the FFT (and inverse FFT) can be used when the detector plane coincides with the so-named diffraction plane or a plane conjugated to it. Otherwise a Fresnel operator is needed.

This is iterated using all images (although some may be left-out due to, for example, image quality problems). The reconstruction is ended when a break-off criterion is met. Such a break-off criterion can be based on the number of iterations, or on the differences in the reconstructed object between subsequent iterations.

It is mentioned that a pixel of the pixelated detector may consist of several radiation sensitive cell added together, commonly called binning.

It is further mentioned that the diffraction plane is a convenient plane to detect the image, as the diffraction plane by definition is the plane where a Fourier transform of the object is formed. However, other planes may be used as well. Those other planes may be planes onto which the diffraction plane is imaged, in which case the FFT may still be used, or it may be other planes, in which case the FFT must be replaced by a Fresnel propagator. In the latter case an estimate of the Fresnel propagator must be estimated as well.

It is noted that it is assumed that the object is a thin object in the sense that the output wave can be calculated as a product of the input wave and the objects' transmission function. As known to the skilled artisan this implies that the amplitude of the resultant complex number is one, and the phase a variable.

A disadvantage of the known method is that for a high resolution reconstruction of the object a pixelated detector with a large number of pixels is needed. The high number of pixels implies small pixels, which in turn necessitate a high read-out speed of the pixelated detector, a high dynamic range and high demands for the signal-to-noise ratio of the detector.

Another disadvantage is that the image of the irradiated area must be completely detected, demanding a large detector. As high resolution results from radiation that is scattered far from the unscattered radiation, for a high resolution reconstruction also a detector with a large size is needed.

Another disadvantage is that trying to cover the whole irradiated area in the detector plane with an insufficient number of pixels of larger size causes insufficiently small field of view for the object and input wave in object plane. It leaves part of the probe outside of the computational area, therefore cause fold-back by aliasing, resulting in failure of convergence or the reconstruction will show artefacts.

The method is also known from international application publication WO2005106531A1 to Rodenburg. It is noted that in this patent application the number of nodes in the wave front in the detector plane is identical to the number of pixels of the detector, and all nodes have a one-to-one relationship, contrary to the method described by Maiden [-1-].

The invention aims to provide an improved method.

To that end the method according to the invention is characterized in that a pixel of the detector image corresponds to more than one node of the second calculation plane, and during the update the measured intensity of each detector pixel is made to match the total intensity of the corresponding number of nodes.

It is remarked that there may be a difference between the number of detector cells and the number of pixels, due to binning of the cells. What is defined here as a pixel, is the minimum area for which an intensity value is measured.

The invention is based on the insight that the resolution of the reconstructed object is based on the number of nodes used in the calculations, but that this does not necessarily need to be a one-to-one relationship between a node in the image plane (the second calculation plane or detector plane) and a pixel of the detector. Instead it suffices that the intensity contribution of several nodes corresponding with the area of one pixel matches the intensity of the pixel.

It is noted that, although no rigid mathematical proof can be given, both the prior art method and the method according to the invention have shown to work with thick objects (where the modules or amplitude is less than one).

It is further noted that, in the case that a node is placed at the boundary of two segments, several "solutions" can be used. Without large deterioration of the model the node can be assigned to one of the pixels, it can be left unchanged (so made dependent on the propagation of the estimate of the output wave to the detector plane only), it can be set to a fixed value, for example to zero, or its intensity can be divided to both pixels using a weight factor. The latter has a physical basis when the detector is based on the generation of electron/hole pairs, and part of the electron/hole pairs are detected in one pixel and part in the other pixel.

When nodes are placed outside of the detection area also several "solutions" can be used. For example, it can be left unchanged (so made dependent on the propagation of the estimate of the output wave to the detector plane only), or it can be set to a fixed value, for example to zero.

In an embodiment the signal of at least one pixel of the detector is disregarded in the iterative update process and the corresponding nodes in the second calculation plane associated with said pixel are not updated during the iterative update process.

This embodiment can be used when one of the pixels is for example a "dead" pixel. By leaving nodes in the second calculation plane (the detector plane) associated with said pixel unchanged, or by setting them to zero, the reconstruction can take place without the (wrong or missing) information of said pixel.

It is noted that other methods of dealing with such pixels can be envisioned, such as setting it to zero. However, this might hamper convergence or it may introduce artifacts.

In an embodiment the iterative update of the object is extended to include updating the probe (the input wave front or short: input wave).

In some cases the probe is sufficiently well-known, and need not be changed (other than that it is shifted over the object). In other cases the method is started with a rough estimate of the probe (for example a Gaussian probe profile, or a top-hat profile), and iteratively this estimated profile is improved to match the actual probe. Mathematical methods for this are known to the person skilled in the art.

In another embodiment the detector plane is the diffraction plane, or an image thereof. As known to the person skilled in the art the image formed at the diffraction plane is the Fourier transform of the object plane. Also images of that plane (also named "planes conjugated to the diffraction plane") are Fourier transforms of the object. Therefore a (fast) Fourier transform can be used for the Fresnel propagator and the estimate of the Fresnel propagator is the FFT. However, another plane may be used to 'capture' the wave front and detect its intensity.

Preferably each pixel of the detector is associated with (or corresponds to) a whole number of nodes in the second calculation plane (the mathematical representation of the image at the detector plane).

In an embodiment the pixels are formed as sectors or segments or parts thereof.

It is noted that in electron microscopy such segmented detectors are commonly used. An example thereof is the so-called 'brightfield/darkfield detector' used in a TEM.

In an embodiment the radiation is radiation from the group of photonic radiation or particulate radiation, the photonic radiation comprising infrared, visible, ultraviolet light and X-rays, and the particulate radiation comprising electrons, neutrons, atoms, and ions.

Ptychography is well-known to the skilled artisan in the field of electron microscopy. It is also well-known to the skilled artisan in the field of x-ray microscopy. The invention is also of interest for the other types of radiation, as ptychography is of interest in the case that the detector is capable to detect intensity, but not the phase of the detected wave front.

In an embodiment updating the mathematical estimate of the object comprises the steps of:
  using the estimate of the object, the estimate of the Fresnel propagator and the estimate of the incoming wave front, to calculate the complex values for the nodes of the second calculation plane,
  for each pixel of the detector, scale the complex values at the nodes of the second calculation plane associated with each pixel so that the detected intensity of a pixel of the detector image matches the integrated intensity of the corresponding nodes of the mathematical estimate of the image in the second calculation plane
  propagate the resulting scaled mathematical estimate of the image back to the object plane,
  update the estimates of the object.

This describes that for each pixel the complex values of the nodes in the second calculation plane associated with that pixel are scaled until the summation (or integrant) of the intensity of the nodes equals the detected intensity measured by the associated pixel. The input wave front (the probe) is updated only when it is insufficiently well known. It may be sufficiently well known due to earlier measurements, due to ptychographic imaging, due to mathematical modelling of the probe taking into account lens errors, or in other ways.

In an aspect of the invention an apparatus equipped with a radiation source and probe forming parts for forming a probe, a programmable controller to control the probe and the relative position between probe and object, and a pixelated detector sensitive to the radiation produced by the radiation source, is characterized in that the controller is programmed to perform any of the previous described methods according to the invention.

It is noted that the probe acts as the input wave. However, as the part irradiated by the probe needs to overlap with other parts, the probe should not have a diameter as small as possible, but rather should show a certain extent.

In an embodiment the radiation source is an electron source and the probe forming parts comprises electron-optical lenses and deflectors, and the detector is a pixelated electron detector.

This embodiment describes an electron microscope equipped to perform ptychography according to the invention.

In another embodiment the radiation source is an X-ray source and the probe forming parts comprise a diaphragm showing an aperture, and the detector is a pixelated X-ray detector.

This embodiment describes an X-ray microscope equipped to perform ptychography according to the invention.

In yet another embodiment the radiation source is a light source and the probe forming parts comprise a near-field scanning optical microscope probe, and the detector is a pixelated light detector.

In an embodiment the pixelated detector comprises a CCD chip or a CMOS chip.

In an embodiment the object is moved with respect to the probe by mechanical scanning.

The invention is now elucidated with figures, in which identical reference numerals refer to corresponding features. To that end:

FIG. 1 schematically shows an apparatus for ptychography,

FIG. 2A schematically shows a prior art flowchart for ptychographic imaging,

FIG. 2B schematically shows a flowchart for ptychographic imaging according to the invention, FIG. 3 schematically shows a segmented detector, FIG. 4A-4C show prior art reconstructed images (showing the phase, as the modulus of the thin object is always one) of the same object using different numbers of pixels using a Transmission Electron Microscope, FIG. 5A-5C show the intensity of the reconstructed (or known estimate of the) probe obtained using the prior art method, FIGS. 6A-6C show the results of object reconstruction using the invention, FIGS. 7A-7C show the reconstructed amplitude (square root of the intensity) at the detector plane per pixel, FIG. 8A shows a set of original (phase of the) object data (simulation data) represented as 512×512 nodes. This results in a detector data set as shown in FIG. 8B, showing the amplitudes of the 512×512 nodes. The phase (in the detector plane) is shown in FIG. 8C. The amplitude (square root of the signal 'measured' by a 16 segment detector) using the simulation input data is shown in FIG. 8D, FIG. 9A shows the reconstructed (phase of the) object using the 16 segment detector and 512×512 nodes for the calculation first plane (object plane) and second plane (detector plane). FIG. 9B shows the reconstructed 512×512 nodes in the detector plane; FIG. 9C the reconstructed phase information (often represented in false colors); and FIG. 9D the summed amplitudes of the nodes associated with a segment of the detector, FIG. 10 schematically shows the 16 segment detector used in the simulation of FIGS. 8A-8D and 9A-9D.

FIG. 1 schematically shows an apparatus for ptychography.

FIG. 1 shows a radiation source 102 forming a beam of radiation 106. The beam of radiation is manipulated (focused) by probe forming means 104. An input wave front 108 is formed on an object 110. The output wave of the radiation that traveled through the object propagates to a pixelated detector 114, where the amplitude of the resulting detector wave front (112) is detected.

By repeatedly acquiring an image of a part of the object, each part overlapping with at least one other part, a set of images is acquired that can be used by a mathematical process for reconstructing the object.

It is noted that for different applications this schematic apparatus may take different forms.

For example, in the case of electron microscopy the radiation source is an electron source (for example a tungsten filament, a Schottky source or a field emitter, and acceleration means for accelerating the electrons to an energy of, for example, between 1 keV and 300 keV), and the probe forming means take the form of a multitude of electron lenses, and may include deflectors to deflect the probe over the object.

For example, in the case of X-ray microscopy the probe forming means may take the form of a Fresnel lens, or may simply consist of an aperture in a diaphragm. Either the lens/aperture, or the object may be moved mechanically so that different parts of the object are irradiated, for example using piezo elements. However, it is also possible to move the X-ray source with respect to the probe forming means, for example by changing the impact position where an electron beam impacts on an anode where X-rays are then generated.

It is noted that in this example the diffraction plane is at infinity. This is close to 'far removed' and thus at a sufficiently large distance from the object the image formed at the detector is almost the diffraction pattern. A drawback may be that the diameter of the image is rather large. By adding a lens between object and detector the diffraction plane can be positioned more conveniently.

FIG. 2A schematically shows a prior art flowchart for ptychographic imaging.

FIG. 2A describes the steps made in the mathematical reconstruction.

In step 200 a number of (overlapping) images are acquired and mathematical estimates of the object, the input wave front and the propagator are made. The mathematical estimate of the object can be a very crude estimate, for example an 'empty' object (all nodes set to one).

It is noted that starting with an empty object comprising only zero's doesn't work.

Also the input wave can be simplified to, for example, a top head approximation. In the case that the image is detected in the diffraction plane the propagator is the Fourier transform.

In step 202 the exit wave, that is: the input wave that traveled through the object, is calculated. The assumption is that the output wave can be calculated as a simple multiplication of the input wave and the object transmission function.

In step 204 the output wave is propagated to the detector plane.

In step 206 for each pixel the square root of the measured intensity is assigned to the node associated with said pixel.

In step 210 these nodes with modified values are propagated back to the object plane.

In step 212 the (complex) representation of the object is updated. If needed, also the input wave (the probe) is updated.

In step 214 a break-off criterion is used to end iteration. The break-off criterion may be the number of iterations, or may be based on the changes between subsequent iterations. If the criterion is met, the outcome is the reconstructed object; otherwise a further iteration is made.

It is noted that, after ending the iterations, there is a reconstructed object, but this need not be a good representation. If the iterations ended due to too many iterations, the method may not have converged. Also, if the changes between subsequent iterations are small, this need not imply that the representation is a good representation.

FIG. 2B schematically shows a flowchart for ptychographic imaging according to the invention.

As can be seen all steps are identical to the prior art method described in FIG. 2a, with the exception of step 208. Instead of assigning measured values to the nodes, for each pixel the intensity of all nodes corresponding to that pixel are scaled together until their summed (integrated) value matches the measured value. This allows the field of view in the object plane to remain large enough to accommodate the entire input wave, unlike the scheme shown in FIG. 2A, where part of the input wave can spill out of the field of view. Thereby the invention addresses the problem when too few detector pixels are used, but the pixels are kept large in the detector plane in order to catch the whole irradiated detector plane area.

FIG. 3 schematically shows a segmented detector.

FIG. 3 shows a segmented detector as seen from the object plane, a plane between radius 300 and 302 is divided in four quadrants 302A, 302B, 302C and 302D. Each of these quadrants is a pixel of the detector. Likewise the area within radius 300 is divided in four quadrants, each quadrant a pixel. The resultant detector thus has a total of 8 pixels.

The pixels forming the inner part may have identical surface area as the pixels surrounding them, or they may have different surface areas. Other segmented detectors may have more than four quadrants between each pair of radii, and/or more radii, thus defining more pixels. However, as will be shown later, with a relatively small amount of pixels the inventors achieved object reconstruction of high quality.

It is noted that this type of detectors is already in use on electron microscopes, as bright field/dark field (BFDF) detectors, where normally the inner pixels (bright field) are used to detect the unscattered beam and the outer pixels (dark field) scattered electrons. However, also detectors with a limited amount of square pixels, arranged in for example an 8×8 grid, can be used.

FIG. 4A-4C show prior art reconstructed images (showing the phase, as the modulus of the thin object is always one) of the same object using different numbers of pixels using a Transmission Electron Microscope. The (simulated) object is a realistic representation of a thin layer of amorphous carbon. The high intensity spikes represent the carbon atoms. The probe used to generate the data set is a (simulated) realistic probe with a spherical aberration of 2.7 mm, opening angle of 7 mrad and defocus of 50 nm from Scherzer conditions, which are very well known to the skilled artisan.

The images are obtained using a simulated set of data measured by a hypothetical detector. No limitation to the dynamic range was made. The size of the detector in each of the image is kept identical, thus capturing a similar maximum scatter angle. However, the hypothetical detectors differ in their number of pixels and the pixel sizes, as the data is binned (the data for several elements of the detector is combined to one pixel), the number of pixels 512×512 in FIG. 4A (binning 1×1), the number of pixels 256×256 in FIG. 4B (binning 2×2), the number of pixels 128×128 in FIG. 4C (binning 4×4). This implies that the number of nodes in the detector plane is different, and thus the angular resolution with which the scatter angle is determined. As the nodes of the mathematical estimate of the object have a one to one relationship with the detector pixels, after inverse transformation the field-of-view of the reconstructed object is highest when using 512×512 pixels, and lowest when 128×128 pixels are used: the reconstructed object is 'enlarged' when the number of pixels are reduced.

The hypothetical detector used in FIG. 4A had 512×512 pixels. The reconstructed (phase of the) object shows a large number of dots.

FIG. 4B shows the result when the identical simulated data set used in FIG. 4A is binned 2×2, resulting in a hypothetical detector with 256×256 pixels. The reconstructed (phase of the) object doesn't show dots anymore, but a number of identical structures, nicknamed "airplanes". This indicates artifacts. Careful analysis shows that the position of the 'airplanes' resemble the position of the dots of FIG. 4A, but enlarged by a factor 2.

FIG. 4C used the same dataset, but now binning is 4×4, resulting in a hypothetical detector having 128×128 pixels. The reconstruction of the (phase of the) object completely failed.

FIG. 5A-5C show the intensity of the reconstructed (or known estimate of the) probe obtained using the prior art method. The reconstructed probe is obtained using a simulated set of data measured by a hypothetical detector. No limitation to the dynamic range was made. The size of the detector in each of the images is kept identical, thus capturing the same maximum scatter angle. However, the hypothetical detectors differ in their number of pixels and the pixel size, as the data is binned (the data for several elements of the detector is combined to one pixel), the number of pixels 512×512 in FIG. 5A (binning 1×1), the number of pixels 256×256 in FIG. 5B (binning 2×2), the number of pixels 128×128 in FIG. 5C (binning 4×4). This implies that the number of nodes in the detector plane is different, and thus the angular resolution with which the scatter angle is determined. As the nodes of the mathematical estimate of the probe have a one to one relationship with the detector pixels, after inverse transformation the field-of-view of the reconstructed probe is highest when using 512×512 pixels, and lowest when 128×128 pixels are used: as in the case of the reconstructed object, the reconstructed probe is 'enlarged' when the number of pixels are reduced.

Figure 1:
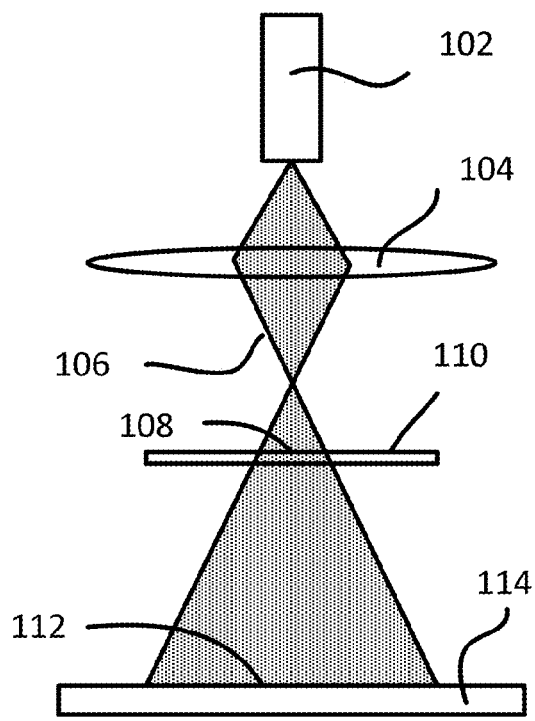
Figure 3:
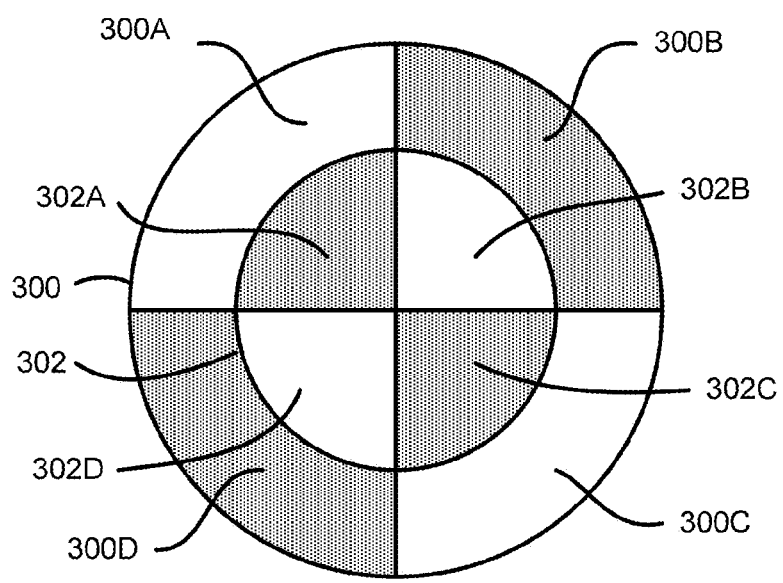
Figures 2A, 2B:
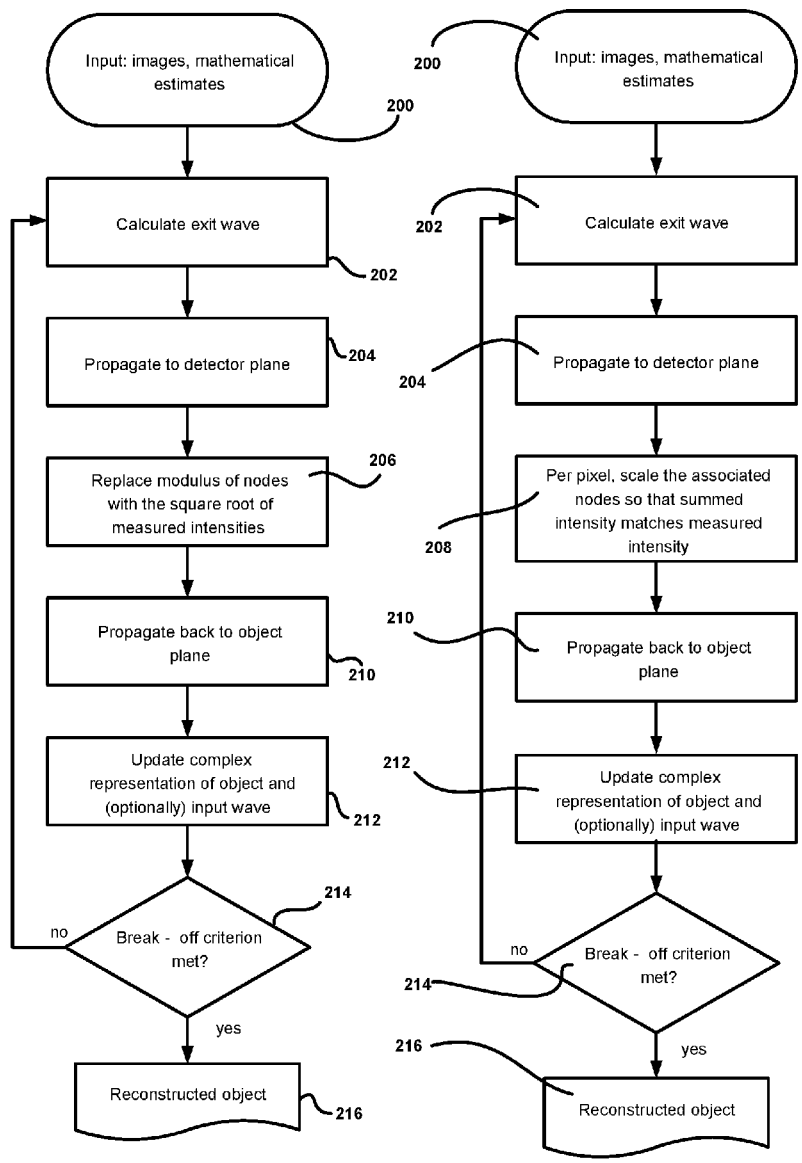
Figure 4A:
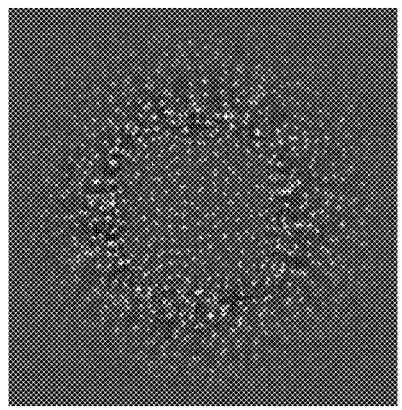
Figure 5A:
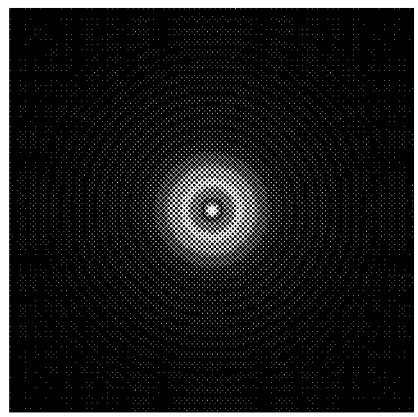
FIG. 5A shows an Airy disk (probe amplitude) that has almost no intensity outside the field of view.
Figure 4B:
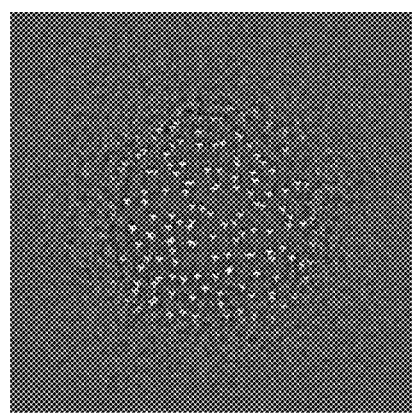
Figure 5B:
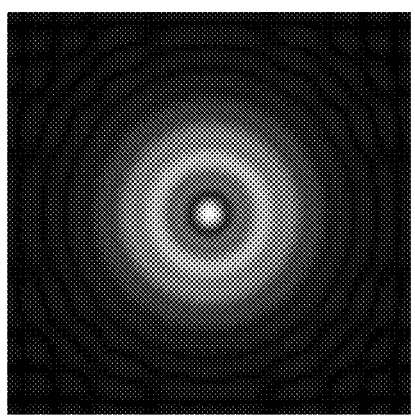
FIG. 5B shows an Airy disk (probe amplitude) that has a small amount of intensity outside the field of view, which is folded back by aliasing.
Figure 4C:
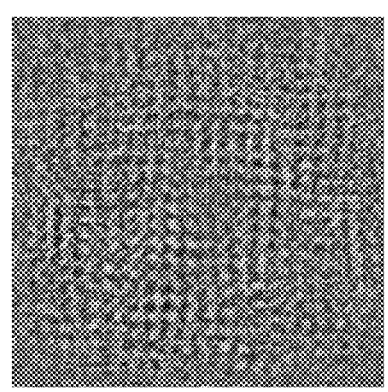
Figure 5C:
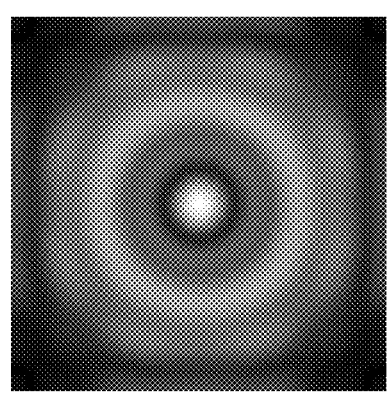
FIG. 5C shows an Airy disk (probe amplitude) that has a large amount of intensity outside the field of view, which is folded back by aliasing resulting in a severely distorted representation of the probe.

FIGS. 4A-4C together with FIGS. 5A-5C show that the prior art method requires a detector with a pixel size and a number of pixels such that it results in a field-of-view in the object plane large enough to accommodate the entire illumination (completely contains the probe), while in the Fourier space (detector plane) it completely covers the data. This is best seen when observing the reconstructed probe. Even the slight spill-over shown in FIG. 5B results in artifacts as shown in FIG. 4B.

Figure 6A:
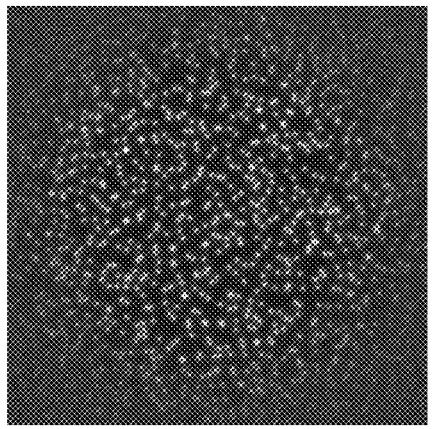
Figure 6B:
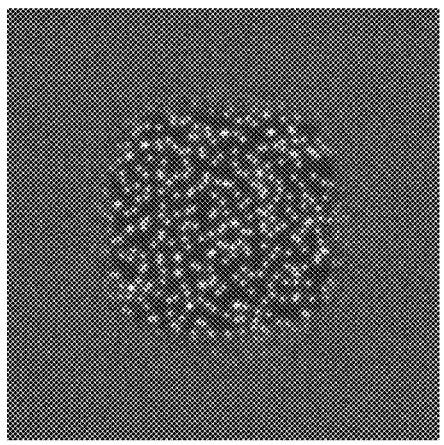
Figure 6C:
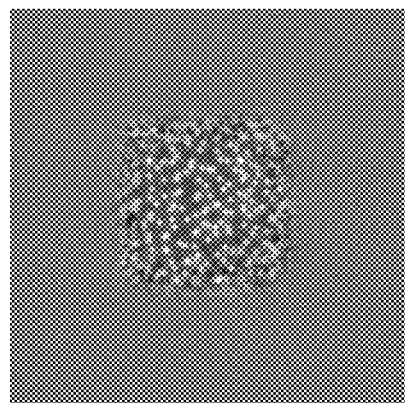

FIGS. 6A-6C show the results of object reconstruction using the invention. The same (simulated) object and (simulated) probe conditions are used as in a previous case.

In the used method the number of nodes in the object plane and the detector plane is kept identical, irrespective of the number of pixels of the detector. The number of nodes is 512×512, the number of pixels in FIG. 6A is 512×512 (no binning), in FIG. 6B 128×128 (binning 4×4) and in FIG. 6C 32×32 (binning 16×16). As the number of nodes is kept identical, all reconstructed images of the object show the same magnification, irrespective of the number of pixels.

The reconstructed (phase of the) object shown in FIG. 6A is comparable to the reconstructed (phase of the) object in FIG. 4A, as is to be expected as the number of pixels used is identical. It is noted that only the phase is shown as for a thin sample the amplitude is one.

The reconstructed (phase of the) object shown in FIG. 6B, using the same number of pixels as the completely failed reconstruction shown in FIG. 4C, still shows excellent results. It is noted that the area of the object that is reconstructed is smaller than in FIG. 6A.

The reconstructed (phase of the) object shown in FIG. 6C, using only 32×32 pixels, also shows excellent results, albeit with a still further limited reconstructed part of the object. Even at this extremely low number (compared to the number of pixels needed in prior art reconstruction) a high quality reconstruction was obtained.

It is noted that a smaller number of pixels does not necessarily imply that the number of calculations is less: the less pixels are used, the more images are needed to come to similar results.

Figure 7A:
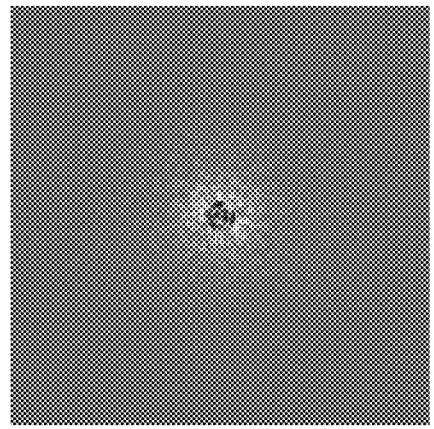
Figure 7B:
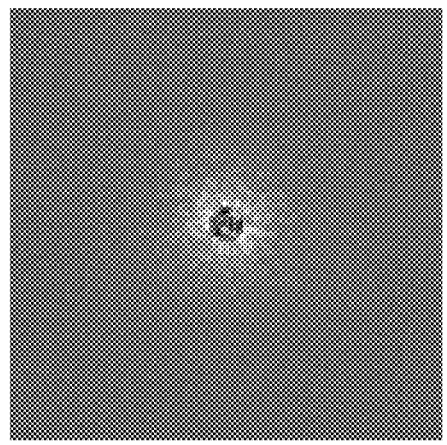
Figure 7C:
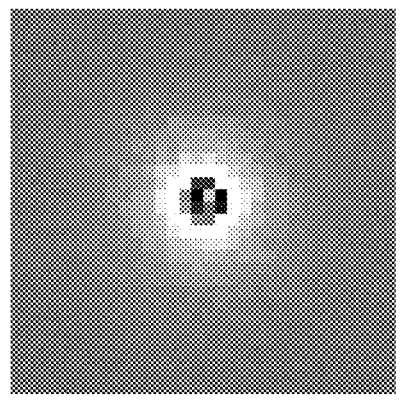

FIGS. 7A-7C show the reconstructed amplitude (square root of the intensity) at the detector plane per pixel. Here again the number of nodes in the object plane and the detector plane is kept identical, irrespective of the number of pixels of the detector.

It is noted that in all reconstructions in the detector data the average bright field contribution is subtracted, as the (summed) bright field intensity is orders of magnitude larger than the summed dark field intensities. This is a direct result of the object being a thin object. As a result of this subtraction the central area appears much darker while clearly showing the small variations in this area. It is further noted that this is no fundamental limitation of the method, and only done for better illustration.

The amplitude is used to make it possible to see the pattern. The intensity (which is the amplitude squared) outside the brightfield disk is otherwise too low to see something even after subtracting the brightfield disk intensity.

The number of nodes is 512×512, the number of pixels in FIG. 7A is 512×512 (no binning), in FIG. 7B 128×128 (binning 4×4) and in FIG. 7C 32×32 (binning 16×16). As the number of nodes is kept identical, all reconstructed images of the object show the same magnification, irrespective of the number of pixels.

The FIGS. 7A-7C show for each pixel the summation of the nodes making up said pixel.

In FIG. 7A no summation is needed, as the number of nodes and the number of pixels is identical, and there is a one-to-one relationship between each pixel and each node.

In FIG. 7B each pixel corresponds to 16 nodes (binning 4×4), and shown is the intensity of the pixels (the summation of all 16 nodes corresponding to said pixel).

In FIG. 7B each pixel corresponds to 256 nodes (binning 16×16), and shown is the intensity of the pixels (the summation of all 256 nodes corresponding to said pixel).

As can be seen the impression of the detected intensities resemble each other, although the graininess of the reconstruction differs (being dependent on the number of pixels). It is noted that comparison of the detector data with the reconstructed detector data showed a high degree of similarity.

Figure 8A:
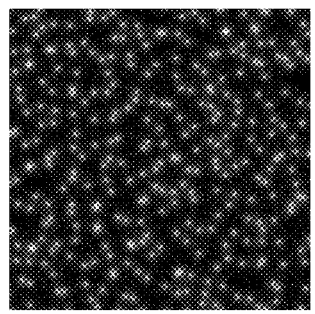
Figure 8B:
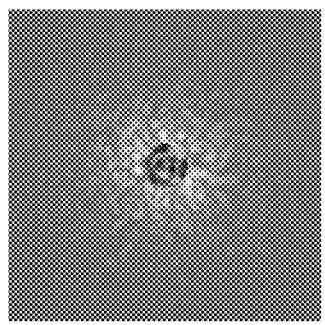
Figure 8C:
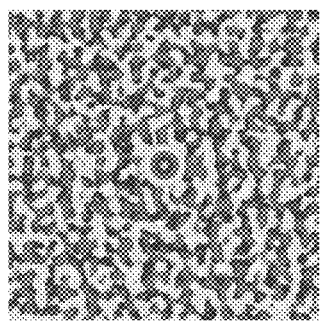
Figure 8D:
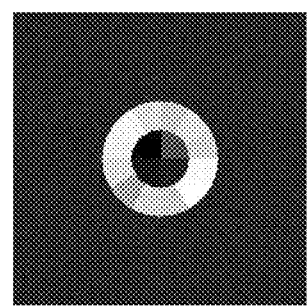

FIG. 8A shows a set of original (phase of the) object data (simulation data) represented as 512×512 nodes. The same (simulated) object and (simulated) probe conditions are used as in previous cases. This results in a detector data set as shown in FIG. 8B, showing the amplitudes of the 512×512 nodes. As the nodes are complex numbers, the simulation input data can also represent a phase. The phase (in the detector plane) is shown in FIG. 8C. These are all simulation input data, and one would hope to get a reconstruction that is close to it, using the data of FIGS. 8B. Normally this would only be possible by a 512×512 pixel detector. However, in this case a 16 segment detector (separately shown in FIG. 10) is used. The amplitude (square root of the signal 'measured' by this 16 segment detector) using the simulation input data is shown in FIG. 8D.

Figure 9A:
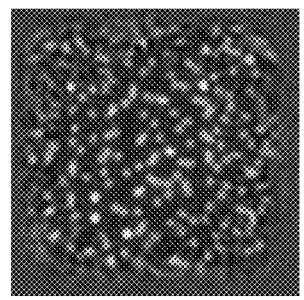
Figure 9B:
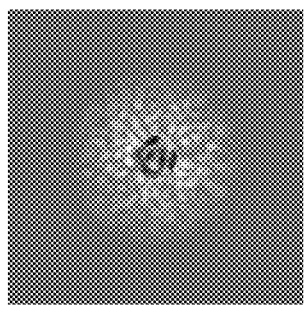
Figure 9C:
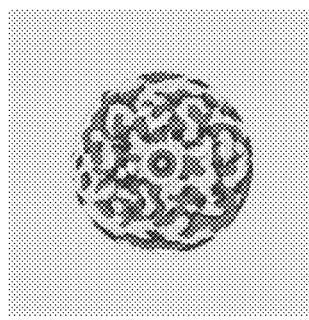
Figure 9D:
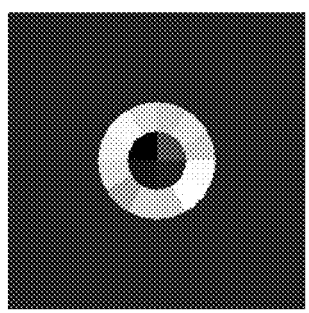

FIG. 9A shows the reconstructed (phase of the) object using the 16 segment detector and 512×512 nodes for the calculation first plane (object plane) and second plane (detector plane). FIG. 9B shows the reconstructed 512×512 nodes in the detector plane, FIG. 9C the reconstructed phase information (often represented in false colors), and FIG. 9D the summed amplitudes of the nodes associated with a segment of the detector.

As can be seen the sharpness of the reconstructed (phase of the) object is a bit less than the original, but (almost) all features can be distinguished. Also the reconstructed amplitude and phase, for the area that can be reconstructed (the detector area) closely resembles the original data. This shows that it is possible with a relatively simple detector (only 16 segments) to reconstruct a high quality representation of the object. It is well-known that the read-out speed for a 16 element detector can be much higher than that of a 512×512 pixel detector. Also, as the area of the segments is much larger, the detected signal will show less signal-to-noise problems, and the dynamic range of the output signal is less, thereby easing the demands for the detector.

Figure 10:
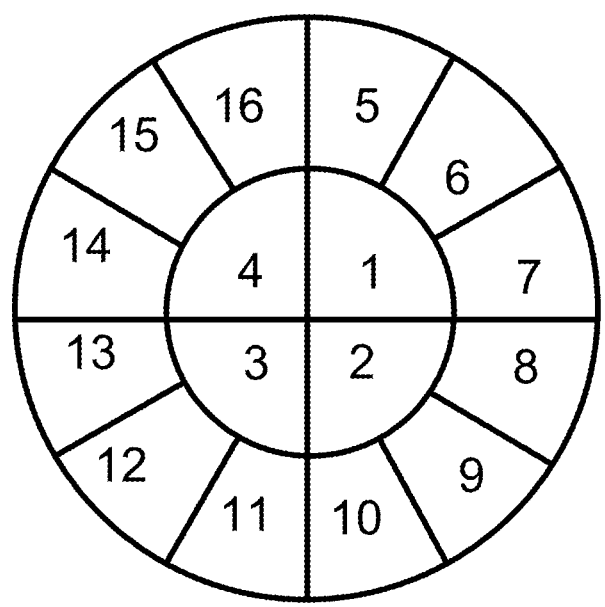

FIG. 10 schematically shows the 16 segment detector used in the simulation of FIGS. 8A-8D and 9A-9D. The detector consists of four inner quadrants 1-4, surrounded by a ring of 12 segments 5-16. Preferably the detector is a silicon device, using photo-diode techniques, or a more elaborate silicon device using boron layers as described in U.S. Pat. No. 8,426,831 B2 to Stoyan, although also a scintillator based detector may be envisioned.

In conclusion, a problem when performing prior art ptychography occurs when the number of pixels is too low. Typically a high number of pixels (after binning) is needed to obtain a high quality reconstruction of an object. Inventors found that, by using calculation planes with more nodes (for example 512×512 nodes) than the number of pixels of the detector, high quality reconstruction of an object can be made, even when using for example a 16 segment detector, or a 32×32 pixel detector. Due to the larger pixel size, thus intercepting a higher flux, the detector demands on for example detector S/N ratio, and dynamic range, are reduced.

CITED NON-PATENT LITERATURE

[-1-] "Superresolution imaging via ptychography", A. M. Maiden et al., J. Opt. Soc. Am. A, vol. 28, no 4 (April 2011), pp 604-612.

The invention claimed is:
1. A method of ptychographic imaging, comprising:
providing an object in an object plane
providing a pixelated detector in a detector plane, the detector plane conjugated to the object plane by a Fresnel propagator, the pixelated detector equipped to detect the intensity of a wave front,
providing a radiation source and probe forming parts equipped to form an input wave front on the object plane, the input wave front transformed to an output wave front by the object, providing a mathematical estimate of the object, an estimate of the Fresnel propagator and an estimate of the input wave front, the mathematical estimate of the object represented by a number of nodes in a first calculation plane, each node a complex value, acquiring at least two images by:
  selecting an area of the object for irradiation,
  irradiating the area with radiation,
  detecting the intensity of a detector wave front on the pixelated detector, resulting in a detector image,
  wherein each irradiated area overlaps with at least one other irradiated area; and iteratively
  updating the mathematical estimate of the object such that, after multiplying the mathematical estimate of the object with the estimate of the input wave front in the first calculation plane and after propagating using the Fresnel propagator to a mathematical estimate of the image represented by a number of nodes of a second calculation plane, the detected intensity of a pixel of the detector image matches the intensity of the corresponding area of the mathematical estimate of the image in said second calculation plane for the at least two images, until a break-off criterion is met, wherein:
  a pixel of the detector image corresponds to more than one node of the second calculation plane, and
  during the update the measured intensity of each detector pixel is made to match the intensity of the corresponding number of nodes.

2. The method of claim 1, the method further comprising iteratively updating the estimate of the input wave front.

3. The method of claim 2, in which the detector plane is a diffraction plane or a plane conjugate to a diffraction plane, and the Fresnel propagator is a Fourier transform.

4. The method of claim 2, in which each pixel of the pixelated detector corresponds to an integer number of nodes of the second calculation plane, the integer larger than one.

5. The method of claim 2, in which the pixels are formed as sectors or segments or parts thereof.

6. The method of claim 2, in which the signal of at least one pixel of the pixelated detector is disregarded in the iterative update process and the corresponding nodes in the second calculation plane associated with said pixel are not updated during the iterative update process.

7. The method of claim 2, in which the radiation is radiation from the group of photonic radiation or particulate radiation, the photonic radiation comprising infrared, visible, ultraviolet light and X-rays, and the particulate radiation comprising electrons, neutrons, atoms, and ions.

8. The method of claim 2, in which updating the mathematical estimate of the object comprises:
  using the estimate of the object, the estimate of the Fresnel propagator and the estimate of the input wave front, to calculate the complex values for the nodes of the second calculation plane,
  for each pixel of the pixelated detector, scale the complex values at the nodes of the second calculation plane associated with each pixel so that the detected intensity of a pixel of the detector image matches the integrated intensity of the corresponding nodes of the resulting mathematical estimate of the image in the second calculation plane propagate the resulting mathematical estimate of the image back to the object plane,
  update the estimates of the object.

9. The method of claim 1, in which the detector plane is a diffraction plane or a plane conjugate to it, and the Fresnel propagator is a Fourier transform.

10. The method of claim 1, in which each pixel of the pixelated detector corresponds to an integer number of nodes of the second calculation plane, the integer larger than one.

11. The method of claim 1, in which the pixels are formed as sectors or segments or parts thereof.

12. The method of claim 1, in which the signal of at least one pixel of the pixelated detector is disregarded in the iterative update process and the corresponding nodes in the second calculation plane associated with said pixel are not updated during the iterative update process.

13. The method of claim 1, in which the radiation is radiation from the group of photonic radiation or particulate radiation, the photonic radiation comprising infrared, visible, ultraviolet light and X-rays, and the particulate radiation comprising electrons, neutrons, atoms, and ions.

14. The method of claim 1, in which updating the mathematical estimate of the object comprises:
  using the mathematical estimate of the object, the estimate of the Fresnel propagator and the estimate of the input wave front, to calculate the complex values for the nodes of the second calculation plane,
  for each pixel of the pixelated detector, scale the complex values at the nodes of the second calculation plane associated with each pixel so that the detected intensity of a pixel of the detector image matches the integrated intensity of the corresponding nodes of the resulting mathematical estimate of the image in the second calculation plane,
  propagate the resulting mathematical estimate of the image back to the object plane,
  update the estimates of the object.

15. An apparatus equipped with:
  a radiation source and probe forming parts configured to form a probe;
  a pixelated detector sensitive to the radiation produced by the radiation source; and
  a controller programmed to perform the method of claim 1.

16. The apparatus of claim 15 in which:
  the radiation source is an electron source;
  the probe forming parts comprise electron-optical lenses and deflectors; and
  the pixelated detector is a pixelated electron detector.

17. The apparatus of claim 15 in which:
  the radiation source is an X-ray source;
  the probe forming parts comprise a diaphragm showing an aperture; and
  the pixelated detector is a pixelated X-ray detector.

18. The apparatus of claim 15 in which:
  the radiation source is a light source;
  the probe forming parts comprise a near-field scanning optical microscope probe; and
  the pixelated detector is a pixelated light detector.

19. The apparatus of claim 15 in which the pixelated detector comprises a CCD or a CMOS chip.

20. The apparatus of claim 15 in which the object is moved with respect to the probe by mechanical scanning.

* * * * *